United States Patent [19]

Haugland et al.

[11] Patent Number: 5,314,805
[45] Date of Patent: May 24, 1994

[54] DUAL-FLUORESCENCE CELL VIABILITY ASSAY USING ETHIDIUM HOMODIMER AND CALCEIN AM

[75] Inventors: Richard P. Haugland, Eugene, Oreg.; Ian C. MacCoubrey, Blacksburg, Va.; Patrick L. Moore, West Roxbury, Mass.

[73] Assignee: Molecular Probes, Inc., Eugene, Oreg.

[21] Appl. No.: 783,182

[22] Filed: Oct. 28, 1991

[51] Int. Cl.$^5$ .......................... C12Q 1/02; C12Q 1/68; C12Q 1/04
[52] U.S. Cl. .......................................... 435/29; 435/6; 435/34; 435/968; 436/800
[58] Field of Search ....................... 435/6, 29, 34, 968; 436/800

[56] References Cited

U.S. PATENT DOCUMENTS 5,001,051  3/1991  Miller ....................................... 435/6

OTHER PUBLICATIONS

Haugland, Handbook of Fluorescent Probes and Research Chemicals, Sets 24 and 28 (1989-1991).
I. C. MacCoubrey, P. L. Moore, R. P. Haugland, *Quantitative Fluorescence Measurements of Cell Viability (Cytotoxicity) with a Multi-Well Plate Scanner*, J Cell Biol 111, 58A (Abstract 303).
P. L. Moore, I. C. MacCoubrey, R. P. Haugland, *A Rapid, ph Insensitive, Two Color Fluorescence Viability (Cytotoxicity) Assay*, J Cell Biol 111, 58A (Abstract 304).

*Primary Examiner*—Michael G. Wityshyn
*Assistant Examiner*—Ralph Gitomer
*Attorney, Agent, or Firm*—Allegra J. Helfenstein

[57] ABSTRACT

This invention relates to a method for simultaneously detecting live and dead cells using two fluorogenic reagents: calcein AM and ethidium homodimer. Live cells are distinguished by an intense uniform green fluorescence generated by the enzymatic hydrolysis of calcein AM:

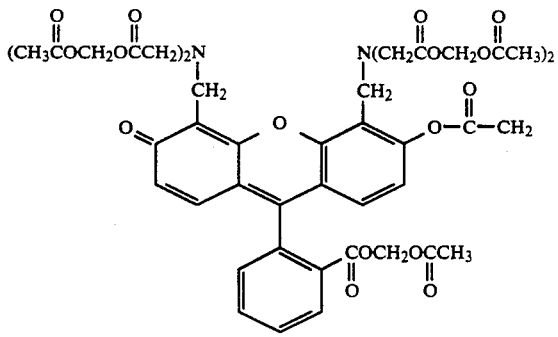

Dead or damaged cells are distinguished by a bright red fluorescence resulting from nucleic acids stained with ethidium homodimer:

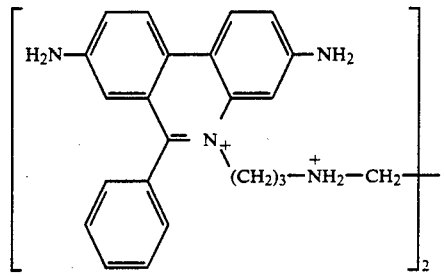

The assay is useful to determine cell viability and to monitor cytotoxicity agents or events.

20 Claims, 4 Drawing Sheets

DUAL-FLUORESCENCE CELL VIABILITY ASSAY USING ETHIDIUM HOMODIMER AND CALCEIN AM

This invention was made with Government support under GM 37347 awarded by the National Institutes of Health. The Government has certain rights in this invention.

FIELD OF THE INVENTION

This invention describes the use of calcein-AM and ethidium homodimer reagents in a two-color fluorescence assay that permits the simultaneous or sequential determination of live and dead cells. The assay is useful to determine cell viability and to monitor cytotoxicity resulting from interaction of the cells with cytotoxic agents or conditions.

BACKGROUND INFORMATION

Evaluation of the viability of biological cells through cytotoxicity measurements is important for assessing the effect of drugs, environmental pollutants, temperature and ionic extremes, radiation and irradiation, other cells and biological modifiers and other potentially adverse factors on cells and tissues. Cell membrane integrity is commonly used to indicate cell viability. Loss of the protective cell membrane results in loss of cell structure, loss of critical intracellular contents, loss of essential ionic gradients and loss of electrical potential. The inevitable result of a major loss of membrane integrity is cell death.

While there is not an exact equivalence between an intact cell membrane and the term "viability" (technically defined as the ability of a cell to maintain its existence), it is common to refer to cells that have intact membranes as "viable" cells and cells where the membrane has been irreversibly disrupted by a cytotoxic reagent as "dead" cells. There is, of course an intermediate condition where a cell that retains its membrane is in the process of "dying". A dying cell is not actually viable in that it cannot be cultured or reproduce. Dying cells are nevertheless often counted as living by common screening tests that rely on cell membrane integrity.

A common feature of loss of membrane integrity is the formation of pores which permit the passage of low molecular weight molecules (MW<2000 Daltons) in and out of the cytoplasm. This enhanced permeability has been the basis of many cell viability and cytotoxicity evaluations. The most common methods in use for cytotoxicity/viability measurements are $^{51}Cr$ release, which uses a radioactive dye, and Trypan Blue exclusion, which uses a colored, non-fluorescent dye.

Fluorescent dyes can be detected with greater sensitivity than can colored dyes and do not have the disposal problems associated with the use of radioactive materials. The combination of different colored fluorescent probes to simultaneously detect live and dead cells is generally described by Haugland, HANDBOOK OF FLUORESCENT PROBES AND RESEARCH CHEMICALS, Set 24 (1989-91). Haugland suggests combining the use of a non-polar membrane permeant derivative that is converted to a polar fluorescent product inside live cells and a polar tracer of another color that is excluded from cells until the membrane is ruptured. Propidium iodide is mentioned as the most common fluorescent polar tracer complementary to those that are retained in live cells, although the reference also notes the potential usefulness of ethidium bromide and ethidium monoazide. Haugland and others have described the use of fluorescein, particularly carboxy fluorescein diacetate, with propidium iodide, for example for use with flow cytometry for sorting live and dead cells.

Two problems with the use of carboxy fluorescein diacetate are leakage from cells following hydrolysis and sensitivity to intracellular pH. Inside living cells, calcein AM is hydrolyzed to a fluorescent dye, calcein, that is well retained by cells, as described in the Haugland reference. The reference does not mention the simultaneous use of calcein AM in combination with any other dye used to detect dead cells. Calcein is less sensitive to intracellular pH than other fluorescein compounds, making it less likely to be quenched in intracellular environments.

Although ethidium homodimer is also described in the Haugland reference (Set 28), the use of ethidium homodimer as a viability stain for cells is not described. Ethidium homodimer has exceptionally high affinity for nucleic acids that is several orders of magnitude greater than ethidium bromide or propidium iodide. It is this high affinity that facilitates the simple, no wash, procedure of this invention. The use of propidium iodide results in unbound dye causing background fluorescence, which usually necessitates washing the cells after combination with the reagent. In contrast, the greater affinity of ethidium homodimer for nucleic acids results in virtually no background fluorescence, thus removing the requirement for washing cells and simplifying and accelerating the assay. The lack of background fluorescence and increased sensitivity related to the use of ethidium homodimer and calcein AM results in a two-color fluorescence assay that can detect fewer cells using a smaller sample. The combination of ethidium homodimer and calcein AM has not previously been suggested as or demonstrated to be suitable for a simultaneous or sequential two-color fluorescence assay of cell viability and cytotoxicity.

DESCRIPTION OF THE DRAWINGS

FIG. 1A shows a significant reduction in calcein fluorescence once a critical saponin concentration is exceeded (LDCD$\approx$2 $\mu$M). FIG. 1B shows a significant increase in ethidium homodimer fluorescence once a critical concentration of saponin is exceeded (LDCD$\approx$1 $\mu$M). Instrument settings (Millipore CytoFluor-2300): Excitation filter: 485$\pm$20 nm; Emission filter: 530$\pm$20 nm, sens. 5; Emission filter: 645$\pm$45 nm, sens. 6.

SUMMARY OF THE INVENTION AND DESCRIPTION OF PREFERRED EMBODIMENTS

This invention provides an improved method for simultaneously or sequentially assessing the viability of cells by using a unique combination of fluorogenic reagents, calcein AM and ethidium homodimer. Following the use of this invention, the cells of a given sample or population are stained either red or green.

"Live" cells, i.e. cells with an intact membrane in which esterase activity is occurring, are distinguished by an intense uniform green fluorescence generated by the enzymatic hydrolysis of calcein AM. Calcein AM has the following structure:

Calcein AM is membrane permeable and virtually non-fluorescent. Once inside the cell, calcein AM is hydrolysed by intracellular esterase activity to yield an intensely fluorescent product, calcein. Calcein is a polyanionic molecule that is well retained within live cells.

Dead cells or cells whose membrane integrity has been damaged are distinguished by a bright red fluorescence resulting from ethidium homodimer binding to nucleic acids. Ethidium homodimer has the following structure:

Ethidium homodimer is excluded from live cells, but the loss of cell membrane integrity allows the dye to enter the cell. The fluorescence of ethidium homodimer undergoes a 40-fold enhancement upon binding to nucleic acids.

Calcein AM and ethidium homodimer are both available commercially from Molecular Probes, Inc., Eugene Oreg. To perform the assay, calcein AM and ethidium homodimer are separately dissolved in fairly polar water miscible solvents, such as DMSO, DMF, ethanol, methanol, or acetonitrile to form a calcein AM stock solution and a ethidium homodimer stock solution. Solvents for calcein AM are limited by the tendency of calcein AM to hydrolyze in the presence of water. Preferably the reagents are dissolved in dry DMSO, usually about 5 mM calcein AM and about 12 mM ethidium homodimer, each in dry DMSO. Stock solutions should be protected from light and from prolonged exposure to room temperature. Preferably, the stock solutions are stored frozen in vials inside a plastic bag containing a desiccant.

Stock solutions of calcein AM and ethidium homodimer are diluted to form working solutions of calcein AM and ethidium homodimer. The working solution of calcein AM should be prepared shortly before use because calcein AM is sensitive to moisture and hydrolyses slowly in aqueous solution, leading to increasing levels of background fluorescence. Ethidium homodimer is more stable and relatively insensitive to moisture. To prepare working solutions, frozen stock solutions are allowed to thaw to room temperature.

Optimal fluorescence measurements are obtained when the reagent concentrations are adjusted for a particular experimental system, i.e. cell type, cell number, dye concentration, temperature, incubation time, and detection system, e.g. fluorescence microscopy, fluorescence well-plate scanner, fluorometer or flow cytometry. Optimization experiments can be performed by separately treating live cells and dead cells with various dye concentrations. Each probe should be optimized separately. Reagent concentrations should be selected that permit a clear distinction between live and dead cells with either probe. Selection of filter sets, instrument sensitivity settings, and the number of cells per test may affect the optimization.

For example, the assay works well with NIH 3T3, PTK$_2$ and MDCK cells using the following conditions: 2.0 μM calcein-AM and 4.0 μM ethidium homodimer in phosphate buffered saline (PBS) incubated at room temperature for 20–40 minutes and evaluated with fluorescent microscopy. Similar experiments with cultured mouse leukocytes (having high esterase activity characteristic of leukocytes) showed that optimum calcein-AM concentration was 5–10× less than that required by the three other cell types. The ethidium homodimer concentration remained the same for all four cell types.

OPTIMIZATION OF REAGENTS

The reagents can be optimized using the following procedure:

1) Test various concentrations of ethidium homodimer between 0.1–10.0μM on dead cell populations. For applications using a fluorescence multi-well plate scanner, it is important to keep the cell number high (approximately $10^3$–$10^6$ cells per mL) and constant. Measure the fluorescence using appropriate filter(s) (see below). Fluorescence measurements should be taken about every 10–15 minutes to provide a time course of staining which can be used to provide optimal incubation times. Select the lowest concentration of ethidium homodimer that stains the nuclei of dead cells bright red without generating significant levels of background fluorescence or bright cytoplasmic staining. For example, 300 μL of 4 μM ethidium homodimer saturates the binding sites in 120,000 killed mouse leukocytes in 45 minutes. Excessive amounts of ethidium homodimer may bind to materials other than nucleic acids, resulting in background signal.

2) Test various concentrations of calcein AM between 0.1–10.0 μM) on dead cell populations. Best results are achieved if all cells have been killed with a lethal treatment known to permeabilize the cell membrane (e.g. a detergent like saponin or a solvent such as methanol). Measure the fluorescence using appropriate filter(s) (see below). Select a calcein AM concentration that results in negligible increases in fluorescence in dead cells. Re-test this selected calcein-AM concentration on live cell populations to ensure that adequate fluorescence is produced by live cells to permit clear detection over background fluorescence. Because of the tendency of calcein AM to spontaneously hydrolyze in aqueous solutions, the concentration of calcein AM should be increased sparingly if live cells are not clearly detected. An increase in the number of cells may also result in a better signal to background ratio, particularly in the plate scanner. Dispersion of calcein AM in aqueous media can be promoted by the addition of a suitable mild detergent with low toxicity, e.g. Pluronic F-127.

3) Determine the extracellular background fluorescence in the assay reagents. In some cases, the addition of a cytotoxic agent may alter the background fluorescence, so appropriate controls that do not contain cells may be required.

PREPARATION OF CELLS

The assay is applicable to a number of cell types. Adherent cells can be cultured on a sterile glass coverslip or in a multi-well plate. For example, fibroblast cells are typically grown on the coverslip or in the wells for 2–3 days until acceptable cell densities are obtained. Cell density is particularly important in ensuring sufficient fluorescent signal for plate scanner applications, preferably approximately $10^3$–$10^6$ cells per mL.

Prior to the assay, the cells may be washed or rinsed gently with 500–1000 volumes of PBS or buffered culture medium containing no colored indicators, to limit the background fluorescence or other artifacts. For example, serum esterase activity due to serum supplemented growth media could cause an unacceptable increase in extracellular fluorescence and colored pH indicators may obscure the fluorescent signal. Adherent cells can be washed in wells or on coverslips. Relatively non-adherent cells, like leukocytes or other suspended cells, can be washed in a test tube and sedimented by centrifugation.

ASSAY PROCEDURE

Working solutions of the reagents for the viability assay can be added to the cells following their transfer to wells, coverslips, or in suspension, with or without washing. Working solutions are prepared from the stock solutions described above. If frozen reagents are used, they should be allowed to warm to room temperature. Preferably, the 12 mM ethidium homodimer stock solution is diluted with PBS to 150 μM, then further diluted to the desired assay concentration. Calcein-AM, however, should be diluted in a single step into the buffer. Aqueous dilutions of calcein-AM should be used within a day. If stock solutions in DMSO are diluted to 1–2 μM calcein AM and 2–4 μM ethidium homodimer, co-solvent concentrations are reduced to $\leq 0.1\%$ DMSO, a level generally innocuous to most cells. To maintain low co-solvent concentrations, stock solutions should not be diluted with DMSO.

To perform the assay, the working solutions of each reagent are combined in an appropriate culture medium with cells or tissue being evaluated and incubated at a temperature suitable for maintaining cell health, usually room temperature. The cells are incubated at least long enough to allow for reagents to yield optimal fluorescence, typically for 5 to 60 minutes. Concentrations of the reagents are chosen so as to give sufficient signal to noise over the background and so that the two color intensities are reasonably matched. Reagent concentrations should be optimized for each cell type, filter selection, and the type of instrumentation, according to the pro Typically concentrations of each reagent below 10 μM are preferred. Following incubation with the reagents, the cells may be washed to decrease the possibility of background fluorescence from the non-specific extracellular binding of ethidium homodimer or from the hydrolysis of calcein AM in aqueous solution. Because of the increased sensitivity of the subject reagents, washing is not required at this point but in some cases may be preferred.

Fluorescence of single cells, tissues or cell suspensions can be detected, and if required quantitated by several means including visual inspection under a microscope, automated or semiautomated fluorescence imaging, flow cytometry, fluorescence spectroscopy in a fluorometer, or in a microplate reader, using the appropriate filter(s).

FILTER SELECTION

Figure 4:
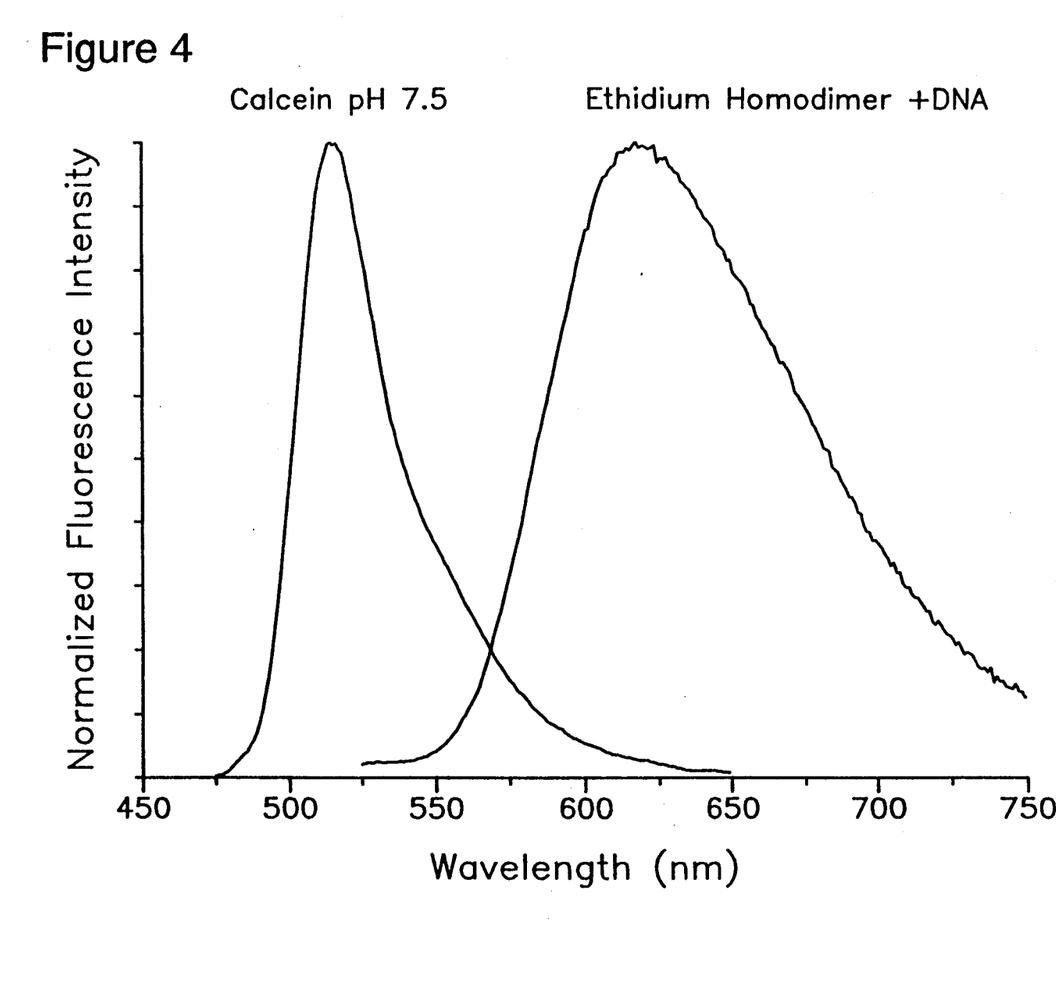
FIG. 4 shows corrected fluorescence emission spectra of calcein and ethidium homodimer (as annotated) excited at 485 nm and normalized at the peak to illustrate the spectral separation of the fluorophores. Sample concentrations are 2.0 μM ethidium homodimer added to calf thymus DNA (50 μg/ml) in pH 7.4 buffer and 1.0 μM calcein in pH 7.5 buffer.

Both fluorophores are excited in the same range as fluorescein (485–500 nm), allowing the use of most commercially available fluorescein filter sets for excitation. A single excitation at less than about 500 nm suffices for excitation of both fluorophores. Both fluorescent dyes when in the cells are readily excited by the 488 nm line of argon laser used in flow cytometry. The emission spectra of the two fluorophores are sufficiently different to permit clear visible or spectrofluorimetric separation of the individual emission (FIG. 4).

Live cells are detected by the green fluorescence from calcein, preferably at a wavelength less than about 530 nm. Dead cells, in contrast, are characterized by red fluorescence of nucleic acid bound ethidium homodimer, preferably at a wavelength of greater than about 600 nm. It is possible to clearly distinguish single cells by their green or red fluorescence using a microscope. This can be accomplished by use of an emission filter that passes all light past about 510 nm. Typically there are no cells with a combination of green and red fluorescence (which would result in a visible yellow fluorescence color) since either calcein or ethidium homodimer but not both can be incorporated in a single cell. This can be confirmed by a cytogram of red versus green fluorescence from a mixed population of live and dead cells analyzed on a flow cytometer.

The green and red fluorescence can be detected sequentially using filters or a monochromator to separate the emission colors and to quantitate their relative intensity. The emissions from each fluorophore can be resolved separately with filters suitable for either calcein (e.g. a fluorescein filter or fluorescent band pass filter centered at 530 nm) or ethidium homodimer (e.g. a fluorescent band pass filter centered at 645 nm).

In fluorescence microscopy applications, labeling of both live and dead cells simultaneously permits the visualization and enumeration of all cells with a single counting procedure. Viability is expressed as a percent of the total number of cells counted. In many cases, such as measuring the effect of cytotoxic agents, it is the relative intensity of green and red fluorescence that is important rather than the absolute magnitude of fluorescence. In fluorescence multi-well plate scanner applications, cell viability is determined as a percent of a maximum signal. Viability can be expressed relative to either probe.

Figures 1, 1A:
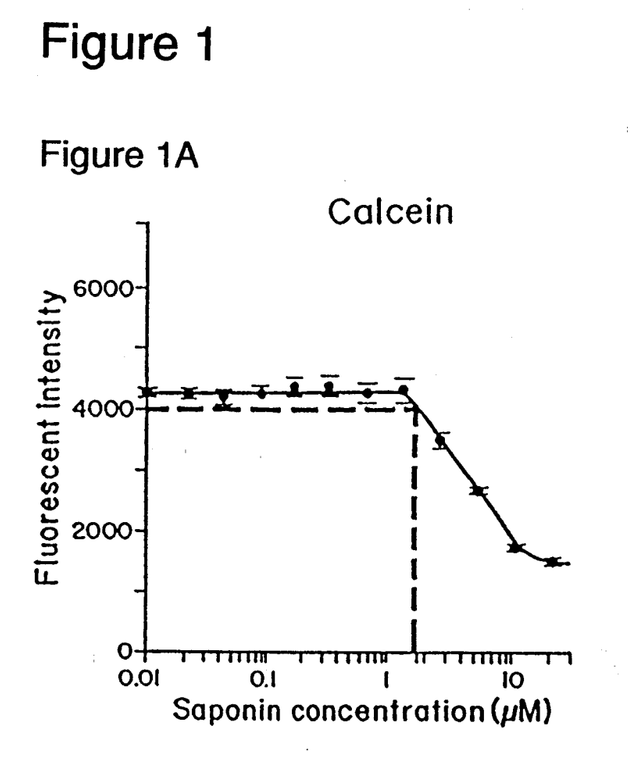
FIGS. 1A and 1B show the dose dependent cytotoxic effect of saponin on a population of leukocytes measured simultaneously with calcein AM and ethidium homodimer on a fluorescence microtiter plate reader. The Lowest Detectable Cytotoxic Dose (LDCD) in the dose at the lower limit of detection (the value along the curve that lies 3 standard deviations away from the zero measurement) and is indicated by the intersection of the dashed lines in each graph.
Figure 1B:
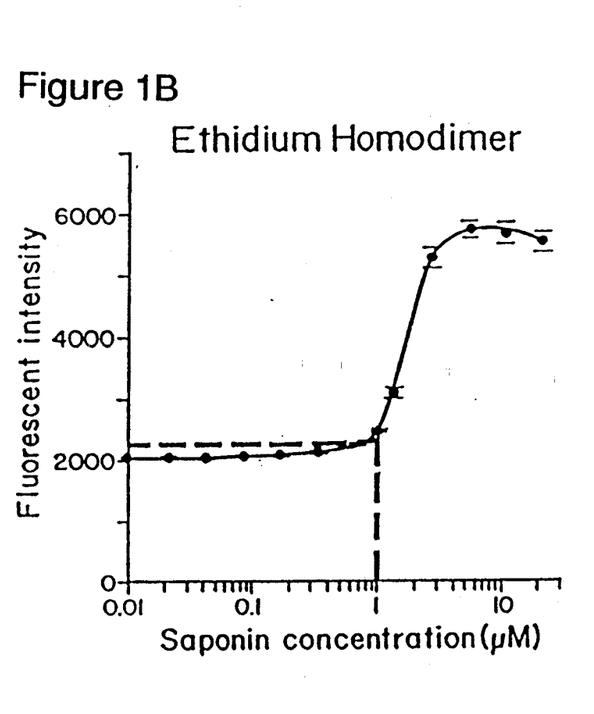
Figure 2:
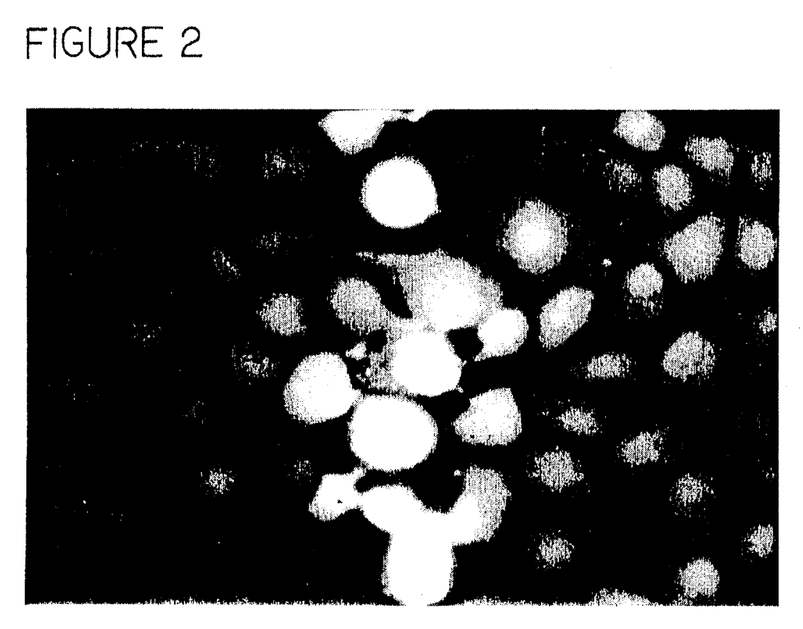
FIG. 2 shows PTK2 cells which were dipped in 50% MeOH/H$_2$O for about 2 seconds and then washed in PBS. The cells were then incubated in PBS containing 12 $\mu$M ethidium homodimer and 5 $\mu$M calcein AM. With the brief exposure to methanol, not all the cells died. The dark cells show green fluorescence indicating live cells, the light cells show bright red fluorescence indicating dead cells.
Figure 3:
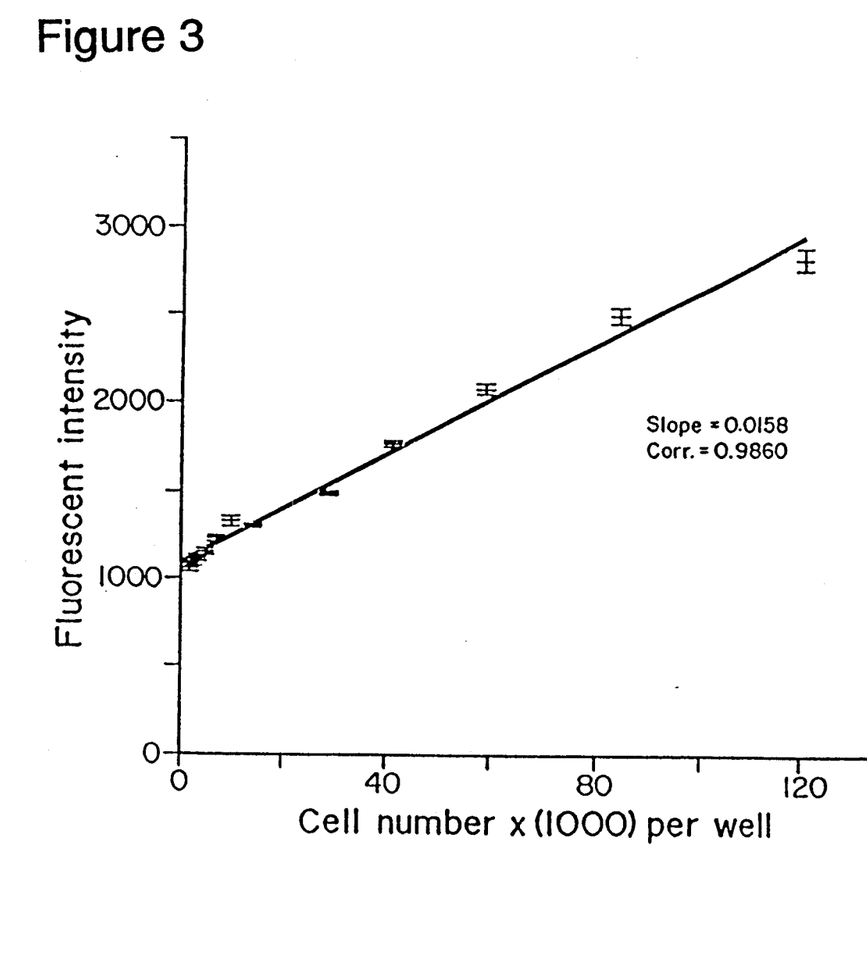
FIG. 3 shows the linear relationship between cell number and fluorescence intensity, obtained by staining dead cells with ethidium homodimer, at or above saturation (4.0 μM ethidium homodimer). Regression analysis indicates a straight line relationship (slope=0.0158; correlation coefficient=0.9860) for cell numbers between 2,000 and 120,000 cells per well. Instrument settings (Millipore CytoFluor 2300): Excitation filter: 485±20 nm; Emission filter: 530±20 nm, sens. 5.

In cell counting applications using the plate scanner, ethidium homodimer is the preferred reagent for estimating the total number of cells because intracellular nucleic acid content is more uniform. The intensity of ethidium homodimer fluorescence at saturation is linearly proportional to the number of killed cells present in a sample (see FIG. 3). This effect permits the fluorescence multi-well plate reader to function as cell counting device. A hemacytometer can be used to count the number of cells in a sample. A sample containing only dead cells can be obtained by contacting the sample with cytotoxic agents in excess of the known lethal dose. Since the nucleic acid content and staining by ethidium homodimer is strongly related to cell number, this technique can be used to calibrate the curve for total or dead cells in a sample.

The intensity of fluorescence of either reagent can be used to measure the effect of a cytotoxic event including exposure to a chemical reagent, the addition of a biological agent, or other change in environmental condition that results in membrane disruption. Many chemical reagents are known to be cytotoxic, including organic solvents, surfactants, toxins, ionophores, drugs, mitochondrial uncouplers, acids and bases, chaotropic ions, enzymatic inhibitors, oxidizing and reducing agents, etc. Biological agents known to be cytotoxic include cytotoxic cells such as cytotoxic T lymphocytes or natural killer cells, complements, some lectins, bacterial or fungal antibiotics or toxins, and others. Conditions known to cause cell death include hyperthermia, hypothermia, freezing, hypoxia, ionizing radiation, light, hypoosmotic and hyperosmotic shock, compression, decompression and others. The effect of a cytotoxic event can be observed over time, or after a fixed period of time.

To measure the effect of a cytotoxic event that involves the addition of a cytotoxic reagent, a stock solution of the reagent is prepared at a concentration greater that what is expected to be a toxic dose and this is added to the cells or tissue in a suitable medium. Typically various concentrations of the reagent are added from 0 to greater than a toxic dose. Toxicity can most conveniently be measured using a fluorescence plate reader such as a Millipore CytoFluor 2300 which has a high capacity for collecting data at two or more wavelengths of emission either for multiple samples in up to 96 wells or in a time based measurement in one or a few wells. Other toxic conditions such as temperature, ionic composition, radiation or cytotoxic cells can be determined by similar measurements.

When a cytotoxic event occurs in a test sample that contains both calcein AM and ethidium homodimer, the green fluorescence from calcein is replaced by the red fluorescence from bound ethidium homodimer indicating that the calcein has leaked from the cells. In the case of a cytotoxic event that occurs after formation of a considerable amount of calcein by the formerly living cells, it may be necessary to wash the cells to reduce the green fluorescence. This is not required in flow cytometry.

Alternatively, the detection reagents may be added subsequent to exposure to the cytotoxic event and the assay to distinguish live and dead cells can be conducted by methods such as described in the following Examples.

The following examples are intended to illustrate general applications of the novel method. These examples are not meant to completely define or otherwise limit the scope of the applications.

EXAMPLE 1

Assay Procedure for Fluorescence Microscopy Applications

A 150 $\mu$M ethidium homodimer aqueous solution is prepared by diluting 25 $\mu$L of the 12 mM ethidium homodimer in dry DMSO stock solution to 2.0 mL by the addition of sterile, tissue culture grade D-PBS (Dulbecco's phosphate-buffered saline: KCl (200 mg/L), $KH_2PO_4$ (200 mg/L), NaCl (8000 mg/L), and $Na_2HPO_4$ (1150 mg/L)). The aqueous solution is vortexed to ensure thorough mixing. A 3.75 $\mu$M ethidium homodimer working solution is prepared by diluting 250 $\mu$L of aqueous ethidium homodimer stock to 10 mL by the addition of sterile, tissue culture grade D-PBS (without $Ca^{2+}$ or $Mg^{2+}$). A 4.0 $\mu$L aliquot of the 5 mM calcein-AM stock solution is then combined with the 10 mL working solution of ethidium homodimer, and vortexed. This gives about 10 mL of a combined reagent solution of approximately 2 $\mu$M of calcein AM and 4 $\mu$M ethidium homodimer.

Non-adherent cells to be evaluated are transferred in suspension to a sterile glass coverslip for incubation in the combined reagent solution. About 100–150 $\mu$L of the combined reagent solution is added to the surface of a 22 mm square coverslip, so that all cells on the coverslip are covered with solution. The cells are incubated for about 30–45 minutes at room temperature in a covered dish (i.e. 35 mm disposable petri dish) to prevent contamination or drying of samples. In some cases, a shorter incubation time can be used if the concentrations of dyes or the incubation temperature is increased. Following incubation, about 10 $\mu$L of fresh combined reagent solution is added to a clean microscope slide. The coverslip containing the cells is quickly transferred to the wet slide. To prevent evaporation, the coverslip is sealed to the glass slide (e.g. with clear fingernail polish). Care should be taken to avoid damaging or shearing cells in the preparation of the slides. The cells are examined under a microscope using blue light excitation at about 480-500 nm collecting light through a long pass filter beyond about 520 nm. Cells with visible green fluorescence are scored as live; those with red fluorescence are scored as dead.

EXAMPLE 2

Assay Procedure for Fluorescence Plate Scanner Applications

A 150 μM ethidium homodimer aqueous solution is prepared and vortexed as in Example 1. A 6 μM ethidium homodimer working solution is prepared by diluting 400 μL of aqueous ethidium homodimer stock to 10 mL by the addition of sterile, tissue culture grade D-PBS (without $Ca^{2+}$ or $Mg^{2+}$). A 6.0 μL aliquot of the 5 mM calcein-AM stock solution is then combined with the 10 mL working solution of ethidium homodimer, and vortexed. This gives about 10 mL of a combined reagent solution of approximately 3 μM of calcein AM and 6 μM ethidium homodimer. Assay reagents are prepared in a concentrated form to allow for the threefold dilution upon addition to the wells.

Adherent cells being evaluated are cultured for 2-3 days in the wells of a microtiter plate to achieve the proper cell density prior to incubation in the combined reagent solution. Each well should contain about $10^6$ cells and about 100 μL of D-PBS. The combined reagent solution is diluted to approximately 1 μM of calcein AM and 2 μM ethidium homodimer by addition of the appropriate amount of combined reagent solution to the wells. The cells are incubated at room temperature for about 30-45 minutes. fluorescence is read on a Millipore CytoFluor 2300 fluorescence plate reader. Excitation of both fluorophores is achieved with the fluorescein filter (485±20 nm). Emissions from each fluorophore are resolved separately with a filter suitable for calcein (530±30 nm; sensitivity 5) or ethidium homodimer (645±45 nm; sensitivity 6).

EXAMPLE 3

Assay Procedure for Flow Cytometry Applications

A 10 mL solution of combined reagents of approximately 3 μM of calcein AM and 6 μM ethidium homodimer, is prepared as described in Example 2. A suspension of single cells in D-PBS at about $10^6$ cells/mL is prepared. A 50 μL aliquot of the combined reagent solution is combined with 100 μL of the cell suspension. The mixture of cells and reagents is vortexed to mix thoroughly and incubated at room temperature for 30-45 minutes. The combination of cells and reagents is analyzed on the flow cytometer, using 488 nm excitation and a 488 nm barrier filter. The light scatter gate is set to include single cells and to exclude clumps. Forward and orthogonal light scatter are recorded, as well as red (>600 nm) and green (520±20 nm) fluorescence.

EXAMPLE 4

Evaluation of a Cytotoxic Event

A 0.04% saponin (Sigma #S-1252) stock solution is serially diluted 1:2 in PBS to yield 10 different dilutions of saponin. Different saponin dilutions in aliquots of 100 μL are added individually to designated wells in a microtiter plate and fluorescence is measured in a Millipore CytoFluor 2300 multiwell fluorescent plate scanner. The final concentrations of saponin in the wells will range from 0 μM to 20 μM after the addition of cell suspensions and fluorogenic reagents.

Cells (J774A.1 Mouse monocyte/macrophage) cultured with Dulbecco's Modified Eagles Media supplemented with 10% calf serum supplement, 2 mM L-glutamine, 10 mM HEPES buffer, 30 μg/mL Gentamicin reagent (all from Gibco Labs), are rinsed with PBS, sedimented by centrifugation, and resuspended in PBS. Cell concentration is adjusted to 2600,000 cells/mL. Suspended cells, in aliquots of 100 μL, are added to the designated wells containing the different dilutions of saponin and incubated for 15 minutes at room temperature.

Stock solutions of 5 mM calcein AM and 12 mM ethidium homodimer are diluted in PBS to yield a 50 mL solution of combined reagents that is approximately 1.5 μM calcein AM and 6.0 μM ethidium homodimer. The combined reagent solution, in 100 μL aliquots, is added to each well and incubated for 30 minutes at room temperature. Fluorescence measurements are made as in Example 2.

EXAMPLE 5

Calculation of Viability Using Signal Magnitude

Fluorescent measurements are obtained according to Example 2. Calcein AM measures live cells according to the formula: % live cells=100% (measured $signal_{530\ nm}$ − minimum $signal_{530\ nm}$)/(maximum $signal_{530\ nm}$ − minimum $signal_{530\ nm}$); where maximum $signal_{530\ nm}$ is the calcein signal from live cell populations, and minimum $signal_{530\ nm}$ is the calcein signal from dead cell populations. Alternatively, ethidium homodimer measures dead cells according to the formula: % dead cells=100% (measured $signal_{645\ nm}$ − minimum $signal_{645\ nm}$)/(maximum $signal_{645\ nm}$ − minimum $signal_{645\ nm}$); where maximum $signal_{645\ nm}$ is the ethidium homodimer signal from dead cell populations, and minimum $signal_{645\ nm}$ is the ethidium homodimer signal from live cell populations.

It is to be understood that, while the foregoing invention has been described in detail by way of illustration and example, numerous modifications, substitutions, and alterations are possible without departing from the spirit and scope of the invention as described in the following claims.

What is claimed is:

1. A method for evaluating the viability of cells in a sample, comprising:
   a) combining a sample containing cells with a concentration of calcein AM sufficient to yield detectable green fluorescence in any live cells present in said sample and a concentration of ethidium homodimer sufficient to yield detectable red fluorescence in any dead cells present in said sample;
   b) viewing the sample with means for detecting the red and green fluorescence of cells.

2. A method, as claimed in claim 1, where said means for detecting fluorescence is fluorescent microscopy.

3. A method, as claimed in claim 1, where said means for detecting fluorescence is a multi-well fluorescent plate scanner.

4. A method, as claimed in claim 1, where said means for detecting fluorescence is flow cytometry.

5. A method, as claimed in claim 1, where said means for detecting fluorescence is fluorescence spectroscopy.

6. A method, as claimed in claim 1, where the concentration of calcein AM is greater than 0 and less than 10 $\mu M$.

7. A method, as claimed in claim 1, where the concentration of ethidium homodimer is greater than 0 and less than 10 $\mu M$.

8. A method, as claimed in claim 6, where the concentration of ethidium homodimer is greater than 0 and less than 10 $\mu M$.

9. A method, as claimed in claim 1, where the sample of cells has been exposed to a cytotoxic event.

10. A method, as claimed in claim 9, where the cytotoxic event is adding an organic chemical reagent or adding a biological agent or a temperature change or a barometric change or any combination thereof.

11. A method, as claimed in claim 10, where the cytotoxic event is adding a biological agent.

12. A method, as claimed in claim 10, where the cytotoxic event is a temperature change.

13. A method, as claimed in claim 10, where the cytotoxic event is a barometric change.

14. A method, as claimed in claim 10, where the cytotoxic event is adding an organic chemical reagent.

15. A method, as claimed in claim 9, further comprising sorting cells exhibiting red fluorescence from cells exhibiting green fluorescence.

16. A method for evaluating the viability of cells in a sample, comprising:
   a) combining a sample containing cells with a concentration of calcein AM sufficient to yield detectable green fluorescence in live cells present in said sample, and a concentration of ethidium homodimer sufficient to stain nuclei in dead cells present in said sample with red fluorescence;
   b) allowing sufficient time for both calcein AM and ethidium homodimer to yield optimal fluorescence;
   c) exciting both calcein AM and ethidium homodimer at less than about 500 nm and greater than about 485 nm; and
   d) viewing the sample with means for detecting the red and green fluorescence in the cells.

17. A method, as claimed in claim 16, where the cells are single cells.

18. A method, as claimed in claim 16, where the concentration of calcein AM is greater than 0.1 $\mu M$ and less than 10 $\mu M$ and the concentration of ethidium homodimer is greater than 0.1 $\mu M$ and less than 10 $\mu M$.

19. A method, for analyzing the viability of single cells, comprising:
   a) combining a sample containing said cells with a concentration of calcein AM sufficient to yield detectable green fluorescence in live cells present in said sample without staining dead cells present in said sample, where the concentration of calcein AM is between 0.1 $\mu M$ and 10 $\mu M$, and a concentration of ethidium homodimer sufficient to stain nuclei in dead cells present in said sample with red fluorescence without staining live cells, where said concentration of ethidium homodimer is between 0.1 $\mu M$ and 10 $\mu M$;
   b) incubating the sample with both calcein AM and ethidium homodimer for 5 to 60 minutes;
   c) exciting both calcein AM and ethidium homodimer at 485–500 nm; and
   d) viewing the sample with means for detecting the red and green fluorescence in the cells.

20. A method as claimed in claim 19, further comprising sorting or counting the live cells or dead cells based on their fluorescence.

* * * * *

UNITED STATES PATENT AND TRADEMARK OFFICE
CERTIFICATE OF CORRECTION

PATENT NO. : 5,314,805
DATED : May 24, 1994
INVENTOR(S) : Haugland et al.

It is certified that error appears in the above-identified patent and that said Letters Patent is hereby corrected as shown below:

On the title page:
In the Abstract, the portion of the first formula reading:

should read

Column 3, lines 40-55, the portion of the formula reading:

should read

Signed and Sealed this

Twenty-fifth Day of October, 1994

Attest:

BRUCE LEHMAN

Attesting Officer

Commissioner of Patents and Trademarks